United States Patent [19]
Svensson et al.

[11] Patent Number: 5,098,397
[45] Date of Patent: Mar. 24, 1992

[54] PERCUTANEOUS ACCESS DEVICE

[76] Inventors: Jan A. Svensson, Solhemsgatan 16, Huskvarna, Sweden, S-561 35; Robert Axelsson, Box 4010, Huskvarna, Sweden, S-561 04

[21] Appl. No.: 572,932

[22] PCT Filed: Jan. 30, 1989

[86] PCT No.: PCT/SE89/00030
§ 371 Date: Sep. 4, 1990
§ 102(e) Date: Sep. 4, 1990

[87] PCT Pub. No.: WO89/06987
PCT Pub. Date: Aug. 10, 1989

[30] Foreign Application Priority Data
Jan. 28, 1988 [SE] Sweden .................. 8800266

[51] Int. Cl.⁵ ............................ A61M 5/32
[52] U.S. Cl. .................. 604/175; 604/174
[58] Field of Search ......... 604/174, 175; 128/897, 128/899; 227/110, 112

[56] References Cited
U.S. PATENT DOCUMENTS

| | | | |
|---|---|---|---|
| 200,471 | 2/1878 | Northrup | 277/112 |
| 3,402,710 | 9/1968 | Poleschuck | 604/175 |
| 4,025,964 | 5/1977 | Owens | 128/889 |
| 4,491,126 | 1/1985 | Cullor | 604/175 |
| 4,668,222 | 5/1987 | Poirier | 604/175 |

FOREIGN PATENT DOCUMENTS 8410727 11/1984 PCT Int'l Appl. .
8706122 10/1987 PCT Int'l Appl. .
1348762 4/1972 United Kingdom .

Primary Examiner—Francis Jaworski
Assistant Examiner—Scott R. Akers
Attorney, Agent, or Firm—Merchant, Gould, Smith, Edell, Welter & Schmidt

[57] ABSTRACT

Device for sterile and leakproof interconnection in a resilient seal (5) enclosed by a cutaneous passageway (1) implanted in the body, of an inner (3) and an outer (2) catheter for supply of a drug or the like from an external container, ampoule or the like to a predetermined locality in the body.

2 Claims, 1 Drawing Sheet

PERCUTANEOUS ACCESS DEVICE

BACKGROUND OF THE INVENTION

The present invention relates to a device for interconnection of an outer catheter having a rigid end portion, and an inner catheter in a cutaneous passageway to be implanted in the body, for supply of drugs or the like. More particularly the invention relates to a cutaneous passageway for interconnection of an internal space inside the body and an external space outside the body, including a resilient, elastic seal enclosed in the passageway and forming a passage therethrough to receive an outer catheter therein, said passage reclosing by withdrawal of the outer catheter therefrom, and screw means for compressing said seal.

A passageway of this type is disclosed in FR-A-2135326.

SUMMARY OF THE INVENTION

In connection with FIG. 6 of the drawings in the international application PCT/SE87/00201 a cutaneous passageway is shown having a catheter for supply for example of a drug to the human body from an external container, ampoule or the like. The supply of a drug must take place under sterile conditions, and a suitable method is to exchange the outer catheter together with the drug container in the cutaneous passageway. This purpose is achieved according to the present invention by the cutaneous passageway having obtained the characterizing features of claim 1.

BRIEF DESCRIPTION OF THE DRAWING

In order to illustrate the invention this will be described in more detail below reference being made to the accompanying drawing in which.

DETAILED DESCRIPTION OF THE PREFERRED EMBODIMENT

The outside shape of the cutaneous passageway 1 appears from the international application PCT/SE87/00201.

Figure 1:
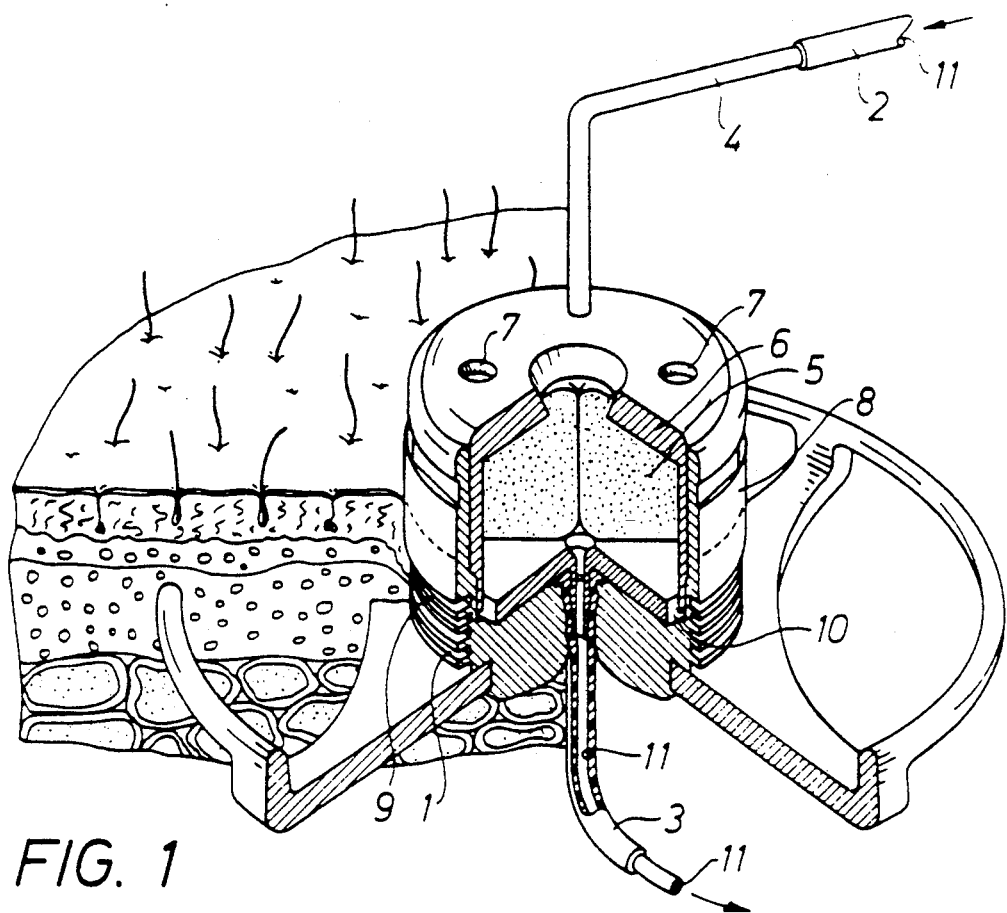
FIG. 1 shows the cutaneous passageway partly cut away, and the location thereof in the body before the outer catheter has been connected to the cutaneous passageway.
Figure 2:
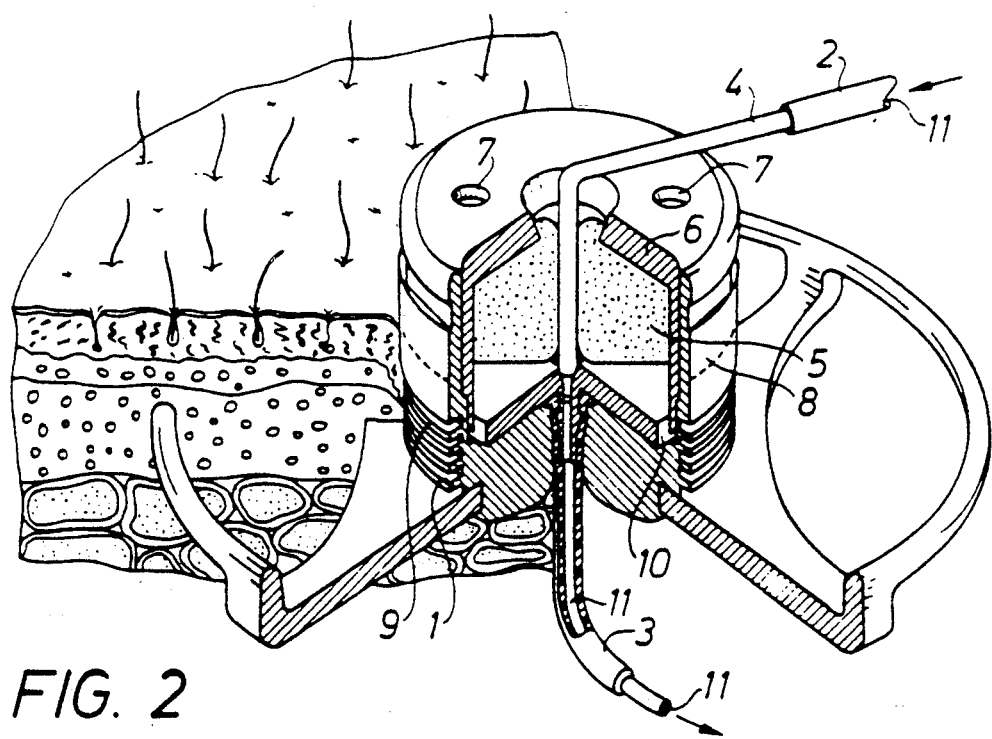
FIG. 2 shows the cutaneous passageway of FIG. 1 but with the outer catheter connected thereto in order to allow communication with the inner catheter.

The novel feature of the present invention is the sealing device in the cutaneous passageway 1, which is shown in FIGS. 1 and 2, in order to supply in a sterile and leakproof manner via catheters 2 and 3 for example a drug to a predetermined locality in the body through the cutaneous passageway 1.

The outer catheter 2 has at the connection end thereof a tube 4 of a rigid material, which is intended to penetrate the seal 5 provided in the cutaneous passageway 1, said seal comprising an elastomer, for example silicone, which recloses and seals when the outher catheter 2 is being exchanged or when the outer catheter 2 has been removed. The seal 5 is kept in place in the cutaneous passageway 1 by a threaded screw cap 6 which is screwed into the outer cylinder 8 which is attached to the base plate 12 of the cutaneous passageway 1 and by means of which the sealing properties in relation to the friction against the connection end 4 of the outer catheter 2 can be controlled. This control is obtained by rotating the screw cap 6 by means of a special tool fitting into recesses 7 in the screw cap 6. The friction against the connection end 4 at the penetration of the seal 5 should be as low as possible so as to prevent the zone 9 for tissue penetration of the cutaneous passageway 1 from coming loose from the body. For the same reason the diameter of the rigid end 4 of the outer catheter 2 should not exceed 3 mm. The seal 5 must also seal against the attachment plate 10 of the inner catheter 3 so as to prevent leakage or passage of bacteria into the passage system 11 of the catheters 2 and 3.

The seal 5 biases the attachment plate 10 against the base of the outer cylinder 8. The seal 5 can be made with a central aperture which is closed by tight fit at the mounting in the cutaneous passageway 1 and forms a guide only for the connection end 4 at the interconnection in the cutaneous passageway 1.

We claim:

1. A cutaneous device for interconnection of an internal space inside the body and an external space outside said body, comprising:

a threaded cylinder substantially open at the top and having a smaller opening at the base;

a subcutaneous base plate attached to said base of said threaded cylinder;

a screw cap with an opening in the top and a threaded portion on the base for engaging with said threaded cylinder;

a resilient, elastic seal enclosed in said screw cap with a passage formed therethrough in alignment with said opening in said top of said screw cap;

an outer catheter having a rigid end portion passing through said opening in said screw cap and said passage, whereby said passage closes when said outer catheter is withdrawn therefrom;

a plate with an opening, interposed between said base of said outer cylinder and said seal, said plate opening in alignment with said passage, a seat formed in the top of said plate adjacent to said opening for receiving the rigid end portion of said outer catheter, whereby said plate forms a support means for said seal and pressure on said seal is increased by advancing said threads of said screw cap onto said cutaneous device; and an inner catheter passing through said opening in said base of said outer cylinder and connected to said opening in the bottom of said plate, whereby said inner catheter is in communication with said passage.

2. The cutaneous device of claim 1, wherein said pressure on said seal is decreased by retracting said threads of said screw cap from said cutaneous device.

* * * * *